(12) United States Patent
Florent et al.

(10) Patent No.: US 7,991,453 B2
(45) Date of Patent: Aug. 2, 2011

(54) MEDICAL VIEWING SYSTEM AND METHOD FOR DETECTING BOUNDARY STRUCTURES

(75) Inventors: Raoul Florent, Ville d'Avray (FR); Lucile Nosjean, Rueil-Malmaison (FR); Pierre Lelong, Nogent-sur-Marne (FR)

(73) Assignee: Koninklijke Philips Electronics N.V, Eindhoven (NL)

( * ) Notice: Subject to any disclaimer, the term of this patent is extended or adjusted under 35 U.S.C. 154(b) by 1110 days.

(21) Appl. No.: 10/534,475

(22) PCT Filed: Nov. 7, 2003

(86) PCT No.: PCT/IB03/05051
§ 371 (c)(1), (2), (4) Date: May 10, 2005

(87) PCT Pub. No.: WO2004/044847
PCT Pub. Date: May 27, 2004

(65) Prior Publication Data
US 2006/0058643 A1  Mar. 16, 2006

(30) Foreign Application Priority Data
Nov. 13, 2002  (EP) .................................... 02292817

(51) Int. Cl.
*A61B 6/12* (2006.01)

(52) U.S. Cl. ........... 600/425; 600/424; 382/128; 378/62
(58) Field of Classification Search .................. 600/417, 600/426, 434
See application file for complete search history.

(56) References Cited

U.S. PATENT DOCUMENTS

| 5,771,895 | A  | * | 6/1998 | Slager ............................ 600/462 |
| 6,413,217 | B1 | * | 7/2002 | Mo ................................ 600/440 |
| 6,532,380 | B1 | * | 3/2003 | Close et al. ..................... 600/431 |

(Continued)

FOREIGN PATENT DOCUMENTS
WO    WO 01/31583 A1 *   3/2001

OTHER PUBLICATIONS

Baert, S. A. M., et al.; 2D Guide Wire Tracking during Endovascular Interventions; MICCAI 2002; 5th International Conference Proceedings; Dohi, T. and Kinnis, R., Eds.; Springer-Verlag Pub.; pp. 101-108.

(Continued)

*Primary Examiner* — Eric F Winakur
*Assistant Examiner* — Vani Gupta (57) ABSTRACT

A medical viewing system for displaying a sequence of medical images that represents moving and/or positioning a guide-wire in a blood vessel, which guide-wire has a guide-wire tip that is contrasted with respect to the guide wire, this system comprising acquisition means that acquires an original sequence of noisy images called live sequence and processing means for processing said live sequence of images in real time, the processing means comprising: first means (10) for automatically detecting the guide-wire tip, yielding skeleton information of the guide-wire tip and a field of motion vectors based on said skeleton information; second means (20) for automatically registering the guide-wire tip with respect to a reference based on the field of motion vectors and for enhancing the guide-wire and the vessel walls while blurring the background in the registered images; and comprising: Display means for displaying a live sequence of processed images.

14 Claims, 5 Drawing Sheets

U.S. PATENT DOCUMENTS

| | | | |
|---|---|---|---|
| 2005/0090733 A1* | 4/2005 | Van Der Lugt et al. | 600/411 |
| 2005/0165303 A1* | 7/2005 | Kleen et al. | 600/424 |
| 2007/0055142 A1* | 3/2007 | Webler | 600/425 |
| 2008/0027313 A1* | 1/2008 | Shachar | 600/424 |
| 2008/0247621 A1* | 10/2008 | Zarkh et al. | 382/130 |

OTHER PUBLICATIONS

Kompatsiaris, I., et al.; Deformable Boundary Detection of Stents in Angiographic Images; 2000; IEEE Trans. on Medical Imaging; pp. 652-662.

* cited by examiner

MEDICAL VIEWING SYSTEM AND METHOD FOR DETECTING BOUNDARY STRUCTURES

FIELD OF THE INVENTION

The invention relates to a medical viewing system for displaying a sequence of images of a medical intervention that comprises moving and/or positioning a tool with respect to a body organ. The invention also relates to a computer executable image processing method to be used in said system. The invention further relates to a medical examination apparatus coupled to such a system. The invention finds for example its application in the medical field of cardiology, for registering and enhancing thin objects of interest such as vessel walls in arteriograms.

BACKGROUND OF THE INVENTION

A method to extract and track the position of a guide wire during endovascular interventions under x-ray fluoroscopy is already known from the publication entitled "2-D Guide wire tracking during endovascular interventions" by Shirley A. M. Baert, in "Medical Image Computing and Computer-Assisted Intervention"—MICCAI 2000, S. L. Delp, A. M. DiGioia, B. Jaramaz (eds), vol. 1935 of Lecture Notes in Computer Science, Springer-Verlag, Berlin, 2000, pp. 727-734. This publication describes a method that can be used in low quality fluoroscopic images to estimate the position of the guide wire in world coordinates. A two-step procedure is utilized to track the guide-wire in subsequent frames. In a first step, a rough estimate of the displacements of the guide wire is obtained using a template matching procedure on a spline model. In a second step, the position of the guide-wire is optimized, by fitting the guide-wire to a feature image in which line-like structures are enhanced. In this optimization step, the influence of the scale at which the feature is calculated and the additional value of using directional information is investigated. The method is applied both on the original and subtraction images. Using proper parameter settings, the guide-wire could be successfully tracked based on the original images, in 141 out of 146 frames from 5 image sequences.

A method for extracting stents in medical images is already known from the publication entitled "Deformable Boundary Detection of Stents in Angiographic Images", by Ioannis Kompatsiaris et alii, in IEEE TRANSACTIONS ON MEDICAL IMAGING, VOL. 19, No. 6, June 2000, pages 652-662. This document describes an image processing method for deformable boundary detection of medical tools, called stents, in angiographic images. A stent is a surgical stainless steel coil that is placed in the artery in order to improve blood circulation in regions where a stenosis has appeared. Assuming initially a set of three-dimensional (3-D) models of stents and using perspective projection of various deformations of the 3-D model of the stent, a large set of two-dimensional (2-D) images of stents is constructed. These synthetic images are then used as a training set for deriving a multi-variate density estimate based on eigenspace decomposition and formulating a maximum-likelihood estimation framework in order to reach an initial rough estimate for automatic object recognition. Then, the silhouette of the detected stent is refined using a 2-D active contour (snake) algorithm, integrated with an iterative initialization technique, which takes into consideration the geometry of the stent. As disclosed in the cited publication, when a narrowing called stenosis is identified in a coronary artery of a patient, a procedure called angioplasty may be prescribed to improve blood flow to the heart muscle by opening the blockage. In recent years, angioplasty increasingly employs a stent implantation technique. This stent implantation technique includes an operation of stent placement at the location of the detected stenosis in order to efficiently hold open the diseased vessel, as illustrated by FIG. 2 of the cited publication. Stent placement helps many patients to avoid emergency heart bypass surgery and/or heart attack (myocardial infraction). The stent, as illustrated by FIG. 1 of the cited publication, is a small, slotted, stainless steel tube cut by a precision laser for forming a coil. It is wrapped tightly around a balloon attached to a monorail introduced by way of a catheter and a guide-wire forming a device called balloon-tipped catheter. This balloon-tipped catheter is introduced into the artery through a small incision. Once in place, the balloon is inflated in order to expand the coil. Once expanded, the stent, which can be considered as a permanent implant, acts like a scaffold keeping the artery wall open. This allows more blood flow to the heart muscle.

SUMMARY OF THE INVENTION

The first cited publication by Shirley A. M. Baert, is focused on guide-wire extraction based on rough estimation using template matching followed by optimization based on threadlike structure enhancement, which is not easy to directly perform in a noisy images. The second cited publication, by Ioannis Kompatsiaris et alii, is focused on visibility of the stent after stent deployment.

However, before introduction of the stent, the doctor encounters a first very difficult step, which consists in passing the stenosis for the first time with the guide-wire. This is one of the most difficult tasks the doctor must perform, because the passage the doctor has to steer through, which is the stenosed part of the artery, is very rough, irregular and limited. Besides, the artery walls are mainly radio-transparent, which may necessitate the use of contrast agent in order to visualize and localize the stenosed part of the artery. When used, contrast agent must be introduced only in very small quantity during very small time duration because it presents toxicity for the patient. So, using contrast agent provides an improved visualization of the artery only during about a dozen of seconds. The doctor must take advantage of this short moment to push the guide-wire forward, with the disadvantage that, due to the contrast agent, he does not see said guide-wire any more. While the contrast agent is operating, the doctor only sees the artery. He anew sees the guide-wire when the contrast agent has been eliminated through the patient's vessel system, after a few moments.

Indeed, this step of introducing the guide-wire for the first time is a very difficult step, due to the bad condition of imaging. The doctor can only follow the intervention on a screen, since in this intervention the rib cage of the patient is not open. The guide-wire for the angioplasty is generally introduced through an opening in the femoral artery and pushed through the arteries until the aortic cross. Beyond the artery cross, the guide-wire is introduced into the coronary that has been diagnosed as suffering of a stenosis. Not only are the guide-wire and the stenosed artery walls observed in noisy fluoroscopic images, but also they show low radiographic contrast that makes evaluation of the guide wire motion very difficult. Besides, during this first phase of the angioplasty intervention, the guide-wire is moving with respect to the artery, the artery is moving under the influence of the cardiac pulses, and said artery is seen on a background that is moving under the influence of patient's breathing and heart beats. These movements make following the guide-wire introduction under fluoroscopic imaging still more difficult to perform. Moreover, these movements make zooming inefficient because the object of interest may get out of the zoomed image frame.

The method of the first cited publication by Shirley A. M. Baert is of no help for localizing the guide-wire with respect to a stenosed part of the artery during the step of first introduction through said stenosed part, since this method estimates the position of the guide in world coordinates and does not provide means to suppress the drawback of the artery motion in the images. The method of the second publication by Ioannis Kompatsiaris et alii, is of no help for localizing the guide-wire during the step of first introduction through the stenosed part of the artery since this method is only focused on visibility of the stent after stent deployment.

Hence, at the difference with the cited prior arts, it is an object of the present invention to propose an imaging system having means to improve the visualization and localization of the guide wire with respect to the artery walls, in real time, based on the detection of the tip of the guide-wire and the registration of the images. This improved means may be used for instance during the first interventional step of guide wire introduction, when the guide wire is passed through the stenosed part of the artery for the first time. This first interventional step of guide wire introduction is very important, because if the interventional step that includes introducing this guide-wire for the first time fails, then the following steps of stent positioning and deployment are no possible. The alternative to the angioplasty is a heavy intervention for bridging the stenosed part of the artery. This heavy intervention comprises opening the rib cage of the patient, which leaves much more after effects than the angioplasty intervention.

According to the invention, these problems are solved by an imaging system having means to process guide-wire tip information for determining the position of all the points of the skeleton of the guide-wire tip, and means to further register the region of interest around said position and means to enhance the visibility of the artery walls and guide wire in said region of interest. This system has means to display in real time the processed images during the angioplasty intervention for the doctor to correctly follow this intervention. This viewing system has processing means comprising tip detection means, registering means, enhancing means and zooming means that permit of accurately visualizing the guide wire with respect to the stenosed artery walls. It is also an object of the invention to provide such a system whose image processing means is user-actuatable.

LIST OF DRAWINGS

Embodiments of the invention are described hereafter in detail in reference to diagrammatic figures wherein:

FIG. 1 is a functional block diagram of the registration means of the imaging system;

FIG. 2A illustrates the guide-wire tip and FIG. 2B the skeletonized guide-wire tip;

DESCRIPTION OF EMBODIMENTS

The invention relates to a viewing system, and to a computer executable image processing method that is used in the viewing system, for detecting, localizing, registering, enhancing and zooming structures in noisy images. The viewing system and the image processing method of the invention are described hereafter in an example of application to the medical field of cardiology. In said application, the object of interest is an artery, which is observed during a medical intervention called angioplasty, in a sequence of X-ray fluoroscopic images called angiograms.

Figure 6A:
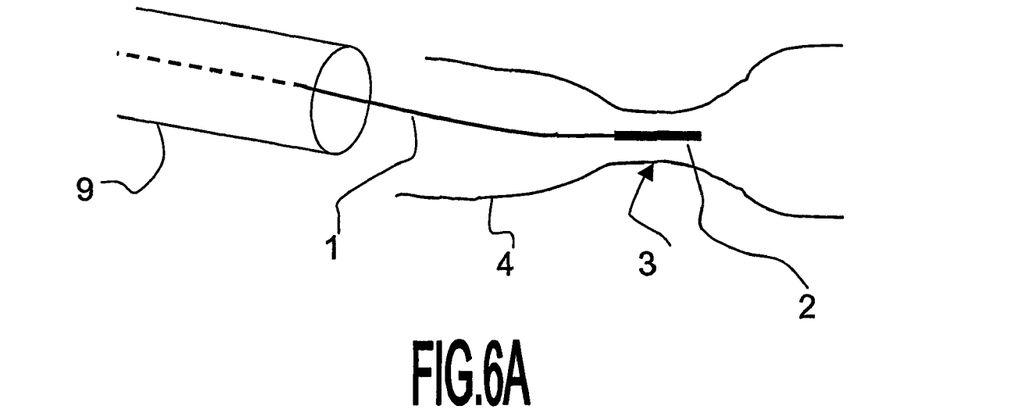
FIGS. 6A and 6B illustrate the step of introduction of the guide-wire tip in an artery.

Referring to FIG. 6A, the angioplasty is a medical intervention that usually comprises several stages for enlarging an artery at the location of a lesion called stenosis. In a preliminary stage, the practitioner localizes a stenosis 3 in a patient's artery 4 as best as possible in peri-interventional images. These images are obtained while using a contrast agent introduced in the artery in order to improve the image contrast and with a conventional dose of x-rays. The guide-wire may be already present, but has not yet been passed through the stenosed part of the artery. Then, the medical intervention is performed while imaged on a screen under fluoroscopy, i.e. with small doses of x-rays. In order to minimize the time duration of the intervention, and the total dose of x-rays to the patient, the intervention must be performed as quickly as possible. Hence, the images must be improved.

After passing a thin guide-wire through arteries until the aortic cross and then towards the stenosed artery 4, using a catheter 9, the angioplasty includes a stage of introduction of said thin guide-wire 1 through the small lumen of the artery portion 3 at the location of the stenosis.

After introduction of the guide-wire, the angioplasty comprises further steps, which are not illustrated, of:
  introduction of a monorail, which is guided by said guide-wire, which has a first balloon wrapped around its extremity, without stent; and positioning said first balloon in the artery portion 3 at the stenosis location;
  inflation of this first balloon for expanding the narrow lumen 3 of the artery 4 at the location of the stenosis; then, removal of the first balloon with the first monorail;
  again using the thin guide-wire 1 for the introduction of a second monorail with a second balloon wrapped around its extremity, and with a stent around said second balloon; and positioning said second balloon with the stent at the location of the stenosis in the previously expanded lumen of the artery 4;
  inflation of the second balloon in order to expand the coil forming the stent, which becomes the expanded stent embedded in the artery wall; and
  considering the expanded stent as a permanent implant, removing the second balloon attached to the second monorail, the guide-wire 1 and catheter 9.

The medical intervention called angioplasty is difficult to carry out. The difficulties arise because of badly contrasted medical images, where the guide-wire, balloon, stent and vessel walls are hardly distinguishable on a noisy background due to the feeble dose of x-rays in fluoroscopy, and are moreover submitted to motions due to the patient's breathing and heart beatings. Some phases of this intervention are very critical. Particularly, the step of passing the guide-wire tip through the artery lumen at the location of the stenosis is very difficult for the doctor and critical for the patient. This is also a key step in angioplasty, since the other steps of angioplasty are not possible without said first step already performed.

Figures 1, 2A, 2B:
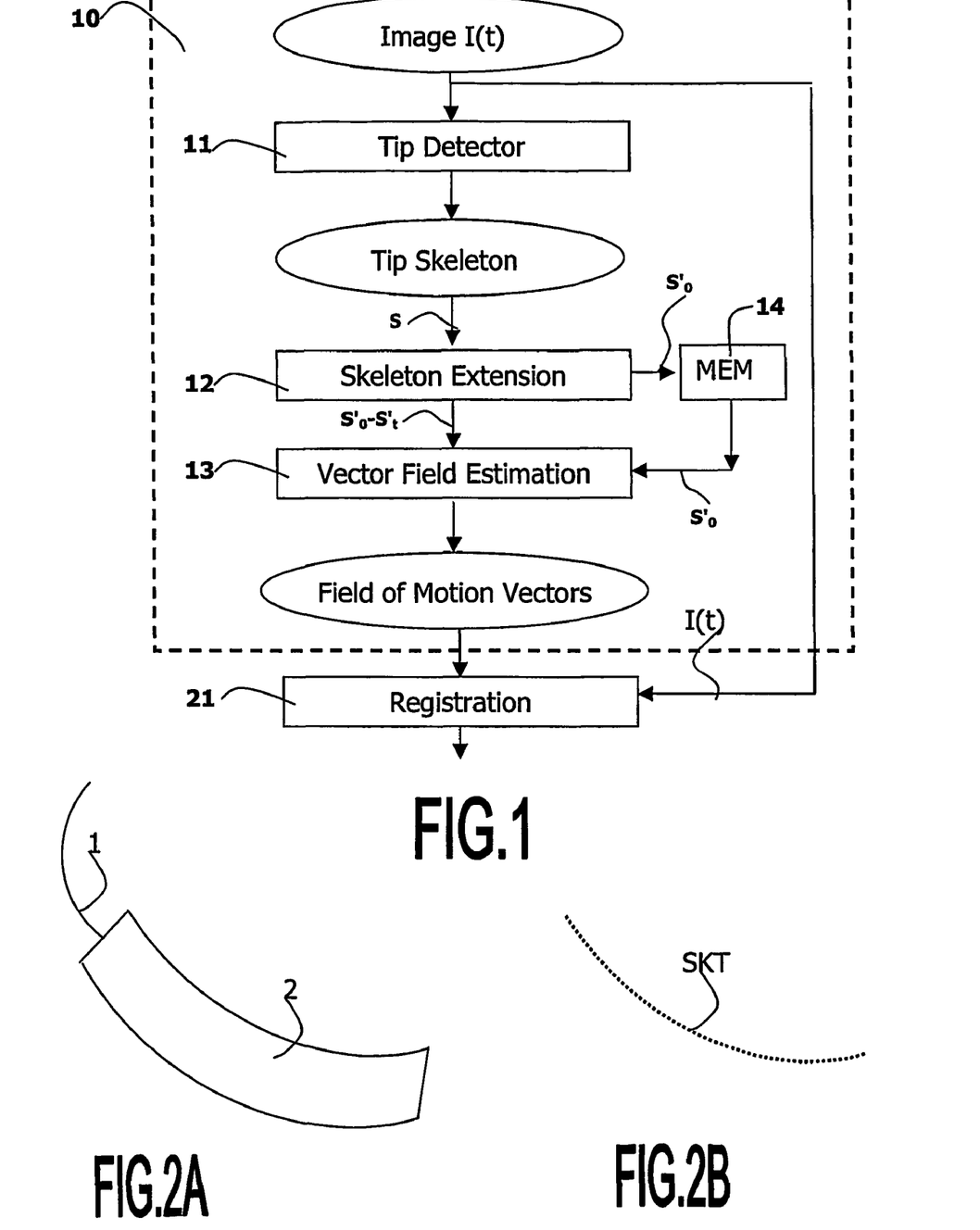

As illustrated by FIG. 2A, the guide-wire tip 2 is a small metallic feature disposed at the extremity of the guide-wire 1. The guide-wire tip is not rigid, but is bendable in order to follow the shape of the artery. This guide-wire tip is about 1 cm to several cm long and is thicker than the guide-wire. The guide-wire tip is very radio-opaque, compared to the artery walls and the guide-wire itself that are hardly distinguishable in the fluoroscopic images and that are difficult to visualize when moving the guide wire forwards inside the artery.

Figure 6B:
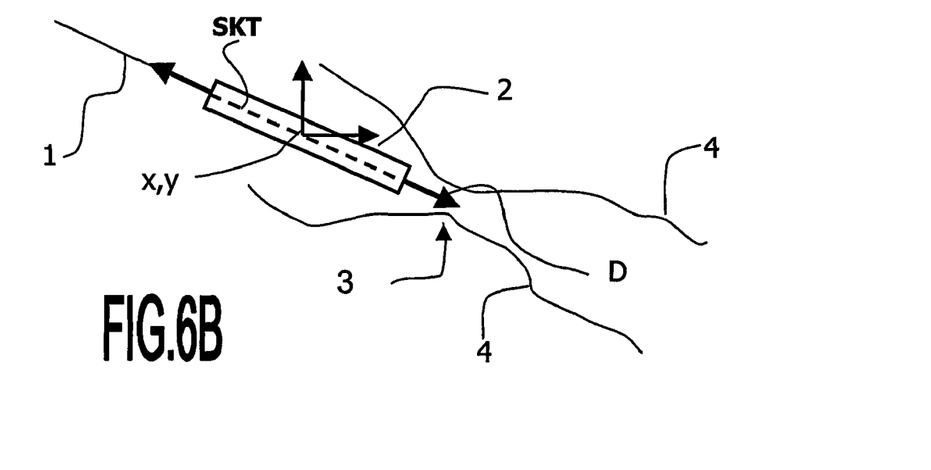

Hence, it has been chosen to use the radio-opaque property of the guide-wire tip in order to localize this feature in a Region Of Interest ROI of the images. The system of the invention has means to detect the guide wire tip, to determine the position of all the points of the skeleton of the guide-wire tip, defined for example by co-ordinates x, y, as illustrated by FIG. 6B, in order to determine a field of motion vectors that is used to register the images with respect to a reference image. The system has further means to enhance and zoom the threadlike structures formed by the guide-wire and the artery walls in the images. In the resulting sequence of images, the contrast of the guide-wire and artery walls is improved, the motion is corrected, zooming may be used to enlarge these structures and the following of the intervention can be substantially continuous. Enhancing the features is of importance for the doctor, since at the beginning it is hardly possible to distinguish anything in the acquired images so that pushing the guide-wire forwards without visibility can disrupt the artery and harm the patient. Registering the images in real time is also particularly important for zooming. The images can be further improved by superimposition of static peri-interventional views and live views. The system of the invention has means to perform all these operations.

The user is the actor of the medical intervention and can have the possibility to intervene at each moment. First of all, the user might choose a Region Of Interest ROI in the images. Besides, the user has at his disposal control means 58, shown in FIG. 4 and FIG. 8, to activate and control the image processing means. These control means 58 comprises starting means, for the user to start the processing operation, to control the duration of the processing operation and to end the processing operation. The processing means 10, 20, denoted by stenosis boosting means, is actuated by the user control 58 during one of the above-cited phases.

Referring to FIG. 1, the system of the invention has first image processing means 10 for providing a field of motion vectors for estimating the motion of the guide-wire tip. The motion estimation is performed in a first Region Of Interest ROI. The means 10 includes a tip detector 11 that solves the problems of automatically detecting the guide-wire tip in the images of the sequence displayed on the screen during the angioplasty. The tip detector provides a skeleton denoted by SKT formed of a chain of pixels. The tip detector 11 may include ridge filter for detecting ridge corresponding to the tip, threshold means to distinguish the tip from other features, pixel gathering means and connectivity analysis means to finally form a chain of pixels as illustrated by FIG. 2B. This tip detection is performed in all the images of the sequence. The skeleton is denoted by $S_0$ in a first image of the sequence to be considered, and is denoted by $S_t$ at a further instant t. The skeleton detection permits of estimating the position of all the points of said skeleton of the guide wire tip in a referential of the images.

An extension of the tip skeleton $S_0$-$S_t$ in the succeeding images of the sequence is then performed by the skeleton extension means 12. This skeleton extension is performed spatially in each image separately. The spatial extension may be performed linearly or according to a curve, in the forward and/or the backward directions. The skeleton may be spatially extended of a length D as shown in FIG. 6B. Information data of the extended skeleton position are denoted by $S'_0$-$S'_t$ in the ROI. Information data of the first extended skeleton position $S'_0$ is memorized in memory means MEM.

Figure 5A:
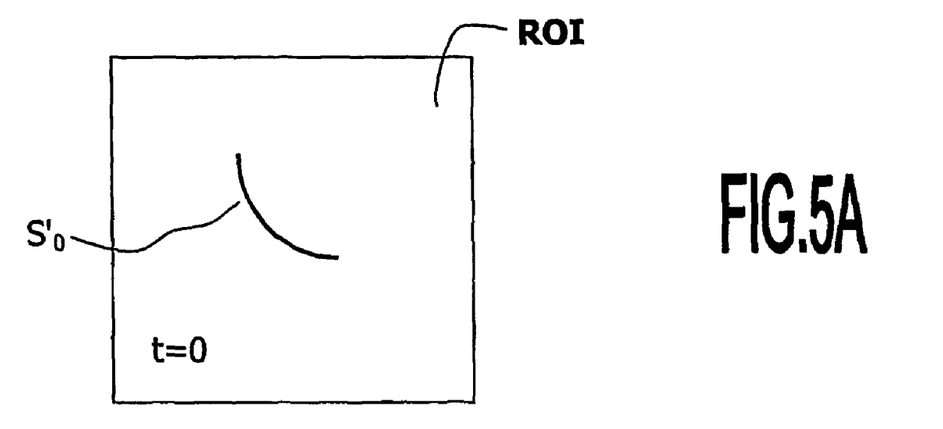
FIGS. 5A, 5B, 5C illustrate the steps of determining motion vectors in a ROI.
Figure 5B:
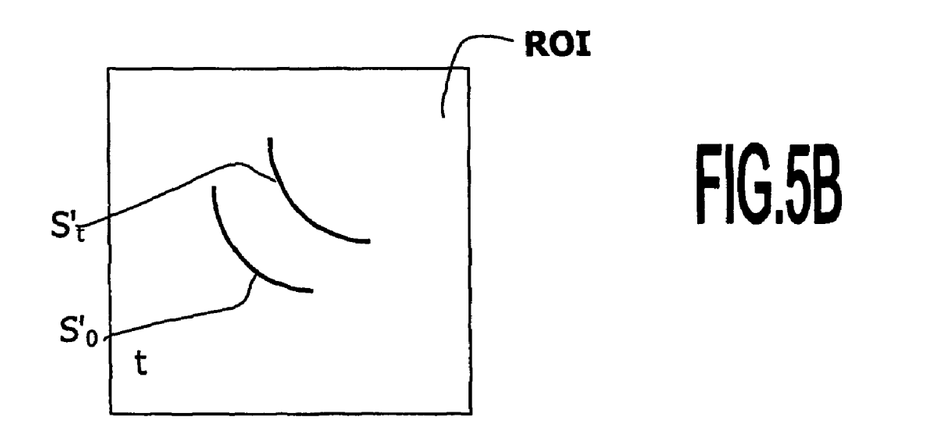
Figure 5C:
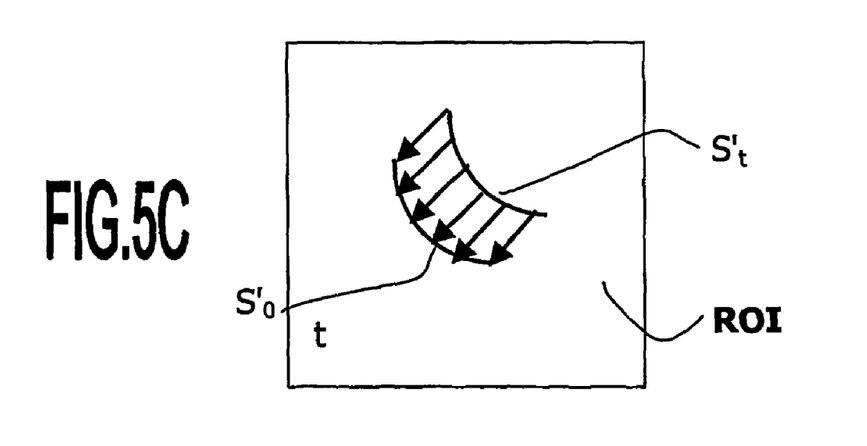

As illustrated by FIG. 5A, 5B, using the information data of the first extended skeleton position $S'_0$ stored in MEM, skeleton vector field estimation means 13 compares the extended skeleton position $S'_0$ at a first instant t=0, in the referential of a first image called reference image, and in the ROI, with the extended skeleton positions $S'_t$ at succeeding instants t. This permits estimating, as illustrated by FIG. 1C, a field of motion vectors V, which makes the extended skeleton positions $S'_t$ correspond to the extended skeleton position $S'_0$. Then a vector field extension is performed by the vector field estimation means 13, for instance using a known technique of warping. Using this technique, a geometric transform is created. Then, said geometric transform is applied for performing a registration operation in the ROI.

Figure 3:
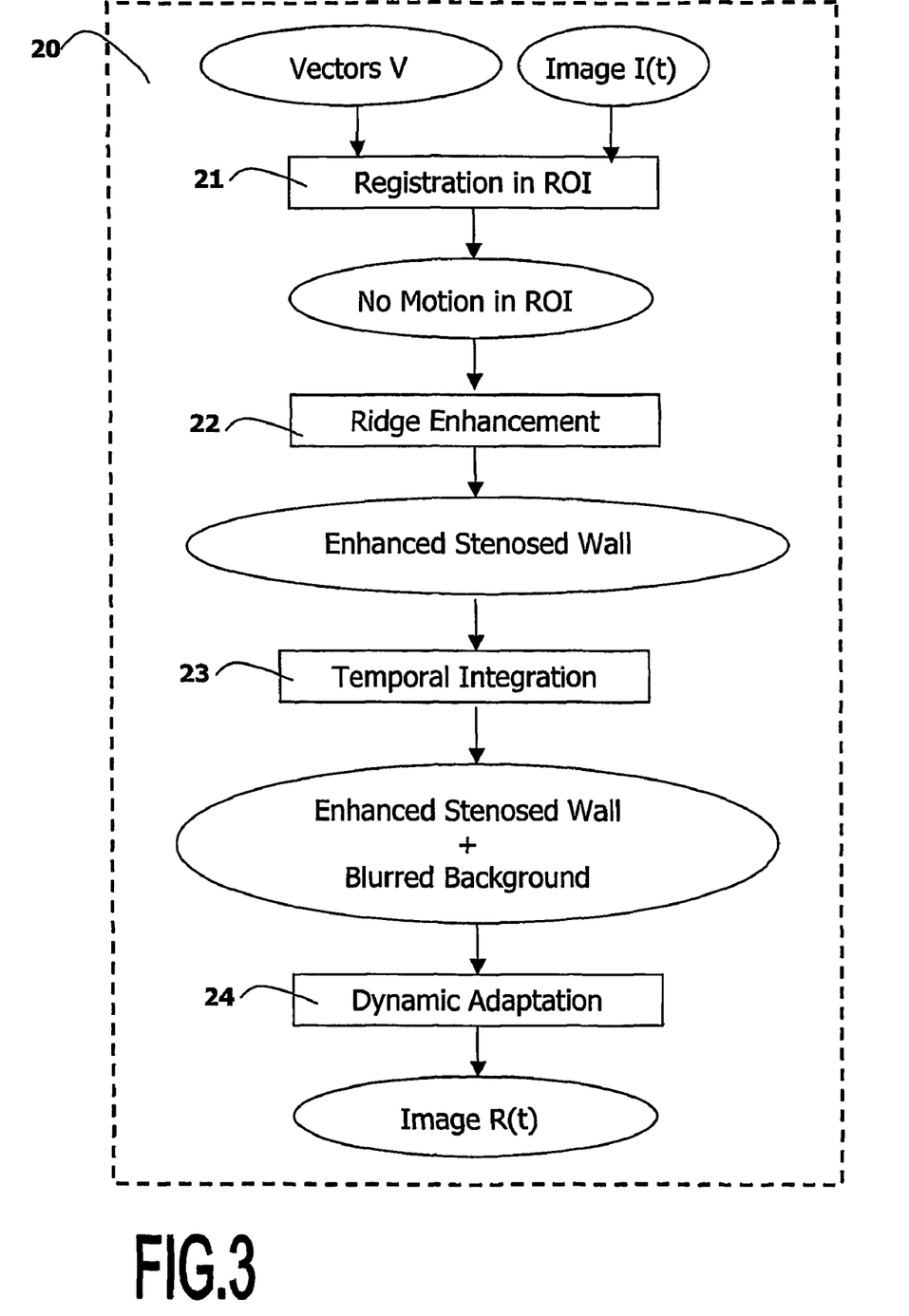
FIG. 3 is a functional block diagram of the enhancement means of the imaging system.

Referring to FIG. 3, the system of the invention further has second means 20 for enhancing threadlike features in the ROI in the image sequence. The means 20 comprises registration means 21 that receives the motion vectors V and the pixel intensity of the original image I(t) and that registers the guide-wire tip in the different images at instants t with respect to the guide wire tip at the instant t=0 considered the referential of the reference image. Since the guide-wire tip moves together with the artery, said artery is also registered with respect to the referential of the reference image and does move any longer from one image to a succeeding image of the sequence. Then, the means 20 comprises ridge enhancement means 22 for enhancing the threadlike structures in the ROI. Hence, the threadlike structures constituted by the guide-wire and the artery walls are enhanced in the ROI. Then temporal integration means 23 performs a temporal integration. Said temporal integration can be achieved by an averaging technique of the pixel intensity of the registered threadlike structures over several images for instance while the background that is still moving is blurred. The temporal integration can be achieved by any other known technique. The means 20 further comprises dynamic adaptation means 24 for providing a resulting image R(t) which may be zoomed according to the need or desire of the doctor.

Figure 4:
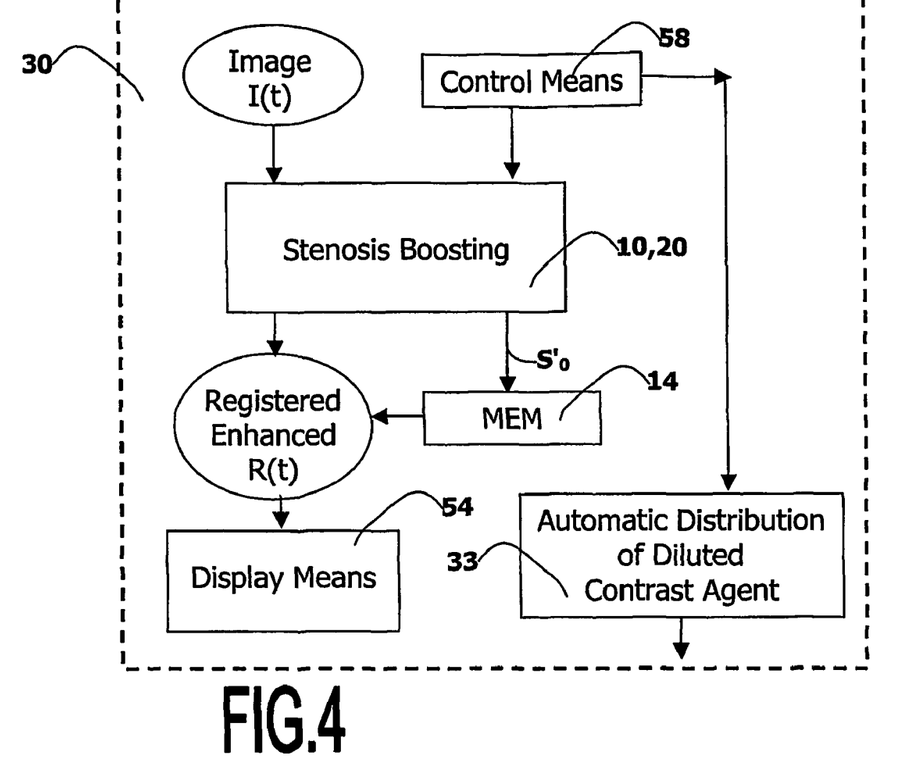
FIG. 4 is a functional block diagram of the general means of the imaging system.

Now, the doctor has means to visualize the artery walls that are no more moving from one image to a succeeding image, that are no more invisible but instead that are enhanced. Referring to FIG. 4, the doctor has the means 58 to start the processing operation called Stenosis Boosting 10,20. When started, the images pass from I (t) to Stenosis Boosting 10, 20. The data that are estimated for registering the ROI in the images, such as $S'_0$, are memorized in MEM, and used for each image registration. From the means 10, the position x, y of all the pixels of the skeleton of the guide-wire tip are estimated. Thus, the doctor can push slowly the guide forward in the stenosed part of the artery, which is registered and enhanced on a blurred background. The start means 58 can start an automatic device 33 for delivering a small amount of contrast agent to be introduced in the artery at appropriate instant with respect to the instants when the doctor pushes the guide forward while observing the processed images R(t). The contrast agent is introduced by appropriate means (catheter). In particular, a great advantage of the invention is that it is no more necessary to inject concentrated contrast agent in the artery of the patient. Since the artery walls are enhanced, the doctor can see sufficiently the position of the artery wall to move the guide-wire properly and safely. However, if the doctor wants to use a contrast agent, it is appropriate to use diluted contrast agent instead of concentrated contrast agent, which permits visualizing the guide-wire tip while the diluted contrast agent is perfusing, which is not possible with concentrated contrast agent. Besides, diluted contrast agent is less toxic for the patient than concentrated contrast agent.

Using diluted contrast agent permits to use it for a longer period of time without inconvenience for the patient, such as a few minutes instead of a dozen of seconds with a concentrated contrast agent. The doctor may operate the start means as often as necessary, until the guide-wire tip is safely passed through the stenosed part of the artery.

Figure 7:
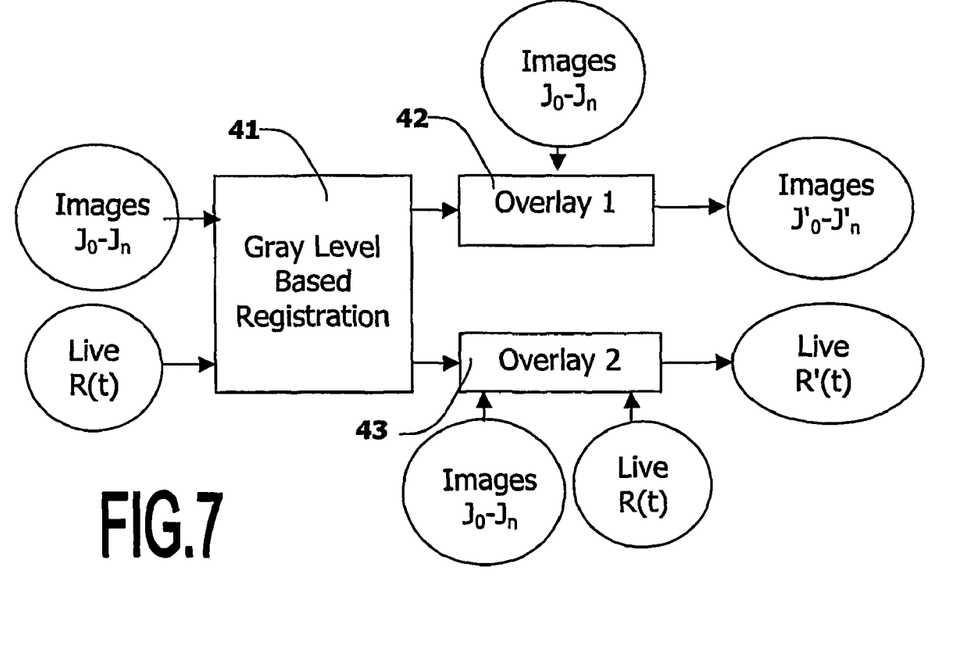
FIG. 7 illustrates the step of overlaying live images and peri-intervention images.

In order to further improve the accuracy of the images to be displayed by the display means for visualization by the doctor, a ROI can be superimposed to a corresponding ROI of a peri-interventional image. Referring to FIG. 7, this operation can be performed using a block-matching technique. The data of the live image R(t) are entered together with data of a sequence of peri-interventional images denoted by $J_0$ to $J_n$ in a gray level based registration means 41. The gray level based registration means 41 can provide the current position of the guide-wire tip as shown in the live image R(t) superimposed on the features of the sequence $J_0$-$J_n$ of peri-interventional images. The resulting combined features form a sequence of peri-interventional images $J'_0$-$J'_n$ denoted by OVERLAY 1 that are enhanced by the features of R(t). Or, using an α-blending technique, the gray level based registration means 41 can provide a live image denoted by R'(t), which is an overlay, denoted by OVERLAY 2, of a peri-interventional image $J_i$ among the set $J_0$-$J_n$, which is determined by the means 41, superimposed on the live image R(t).

Hence the system of the invention is able to provide live images that are registered with respect to one another, resulting in live enhanced images. This system is also able to provide live images that are registered with respect to peri-interventional images.

In a preliminary step, the peri-interventional images can be registered one with respect to another in a referential formed by patient's breathing characteristics and ECG points. These peri-interventional images are then seen as a cloud of points in this referential. Hence, an image I(t) would not be easily matched to one image of this set of peri-interventional images. Now, according to the invention, it is not the image I(t) that is proposed to be matched to one image of the set of peri-interventional images, but instead it is the registered and enhanced image R(t). Hence, a robust registration between the live and the peri-interventional images can be obtained.

Figure 8:
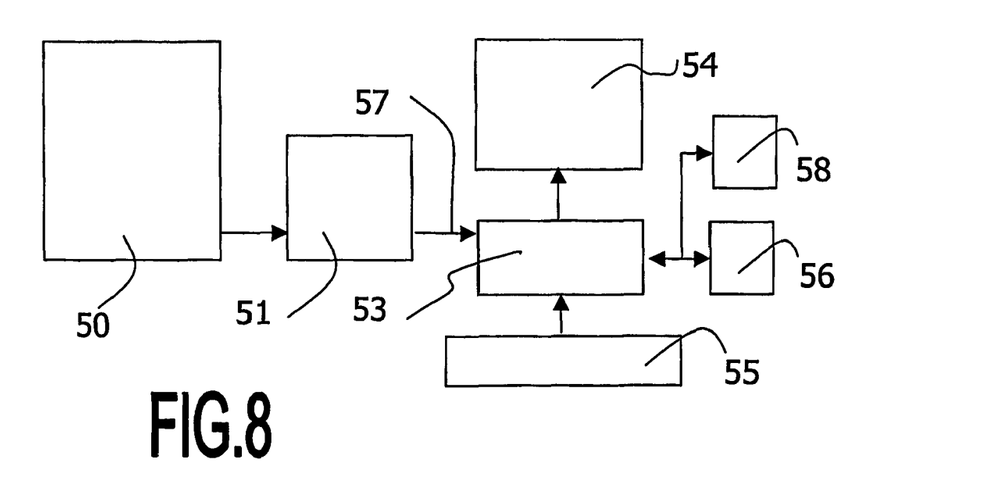
FIG. 8 is a functional block diagram of a medical examination apparatus using said system.

FIG. 8 shows a diagram of a medical examination apparatus 50. The apparatus has means 51 for acquiring digital image data of a sequence of images, and is coupled to a medical viewing system 53 as described above, for processing these data according to the processing method cited above. The medical viewing system is generally used in the intervention room or near the intervention room for processing real time images. Steps of the present method can be applied on stored peri-interventional images, for example for estimating medical parameters. The medical examination apparatus provides the image data by connection 57 to the system 53. The system provides processed image data to display means and/or storage means. The display means 54 may be a screen. The storage means may be a memory of the system 53. Said storage means may be alternately external storage means. This image viewing system 53 may comprise a suitably programmed computer, or a special purpose processor having circuit means such as LUTs, Memories, Filters, Logic Operators, that are arranged to perform the functions of the method steps according to the invention. The system 53 may also comprise a keyboard 55 and a mouse 56. Icones may be provided on the screen to be activated by mouse-clicks, or special pushbuttons may be provided on the system, to constitute control means 58 for the user to start, to control the duration or to stop the processing means of the system at chosen stages or phases.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A computer executable image processing method for displaying in a medical viewing system a sequence of medical images that represents moving and/or positioning a guide-wire in a blood vessel, the method comprising:
    acquiring a sequence of noisy images of the blood vessel and the guide-wire as the guide-wire moves in the blood vessel;
    processing the sequence of noisy images in real time, the processing comprising:
        detecting automatically the guide-wire tip;
        identifying a skeleton of the guide-wire tip including a series of pixels along a centerline of the tip;
        determining field of motion vectors based on said skeleton;
        registering automatically the guide-wire tip with respect to a prior reference image of the sequence of noisy images based on the field of motion vectors;
        integrating temporally by averaging pixel intensity over a plurality of the noisy images of the sequence of noisy images that are registered to the reference image, thereby enhancing the blood vessel and blurring background; and
    displaying the processed sequence.

2. The computer executable image processing method of claim 1, wherein the integrating step including integrating the centerline of the tip to generate a ridge or line depicting the guide wire.

3. A non-transitory computer readable storage medium comprising executable instructions for carrying out an image processing method for displaying in a medical viewing system a sequence of medical images that represents moving and/or positioning a guide-wire in a blood vessel, wherein the instructions, when executed, perform a method to:
    acquire an original live sequence of noisy images called a live sequence;
    start an automatic device to deliver diluted contrast agent into the blood vessel;
    process the live sequence of noisy images in real time, the processing comprising for each most recently acquired noisy image of the live sequence:
    detect automatically the guide-wire tip;
    generate a skeleton of the guide-wire tip comprising a series of pixels along a centerline of the tip;
    generate field of motion vectors based on said skeleton;
    register automatically the guide-wire tip with respect to a prior reference image from the live sequence based on the field of motion vectors;
    enhance the guide-wire and vessel walls while blurring background by integrating temporally by averaging pixel intensity over the most recently acquired image registered to the reference image and a plurality of preceding noisy images of the live sequence registered to the reference image, thereby enhancing the blood vessel adjacent the tip, blurring the background, and enhancing a line corresponding to the tip centerline in the integrated most recently acquired and preceding noisy images; and
    display the processed live sequence.

4. A method for positioning a guide-wire in a blood vessel, which guide-wire has a guide-wire tip that is contrasted with respect to the guide-wire, the method comprising:
  operating a medical viewing system to acquire an original sequence of noisy images called a live sequence;
  processing the live sequence of images in real time, the processing comprising:
    detecting the guide-wire tip, yielding a skeleton of the guide-wire tip comprising a series of pixels along a centerline of the guide-wire tip, and field of motion vectors based on the skeleton;
    delivering diluted contrast agent into the blood vessel;
    registering the guide-wire tip with respect to a reference based on the field of motion vectors;
    integrating temporally by averaging pixel intensity over several images to enhance the images of the guide-wire and the vessel walls while blurring background in registered images; and
    displaying a live sequence of processed images.

5. A medical viewing system for displaying a sequence of medical images that depict moving and/or positioning an imageable tip of a guide-wire in a blood vessel, the system including:
  one or more processors programmed to:
    acquire a sequence of noisy images of a region of interest of a patient depicting the imageable tip of the guide-wire, the blood vessel in which the guide-wire is disposed, and background outside the blood vessel,
    detect the guide-wire tip in each acquired noisy image,
    define a series of pixels along a center line of the tip,
    calculate a field of motion vectors defining motion of the tip in each most recently acquired noisy image relative to a previously acquired reference noisy image,
    register the guide-wire tip with respect to the previously acquired reference noisy image based on the field of motion vectors,
    combine the most recently acquired noisy image of the sequence with a plurality of previously acquired noisy images of the sequence which have been registered to the reference noisy image such that the tip of the guide-wire and walls of the blood vessel adjacent the guide-wire tip are enhanced while the background is blurred, and the center lines of the tip and the most recently and previously acquired noisy images define a line; and
  a display which displays each most recently acquired noisy image combined with the plurality of previously acquired noisy images in real time to provide the sequence of medical images depicting movement of the guide-wire through the blood vessel with the vessel walls enhanced.

6. The system of claim 5, wherein the calculating the motion vectors includes, with the one or more processors:
  spatially extending the centerline in the most recently acquired noisy image with the centerline of a previously acquired noisy image;
  matching the centerline in the most recently acquired noisy image;
  estimating the motion vectors based on the matching of the centerlines.

7. The system of claim 6, wherein combining the most recently acquired noisy image with the plurality of previously acquired registered noisy images includes, with the one or more processors:
  applying the motion vectors to the full most recently acquired noisy image such that the guide-wire tip and the vessel walls of the most recently acquired noisy image are registered with the guide-wire tip and the vessel walls of the plurality of previously acquired registered noisy images and the background of the most recently acquired noisy image and the background in the plurality of previously acquired noisy images are misaligned such that in combining the registered most recently acquired noisy image with the plurality of previously acquired registered noisy images, the vessel walls are enhanced and the background blurred.

8. The system of claim 5, further comprising:
  a user operated control by which a user activates the image acquisition device to acquire noisy images, starts the one or more processors to start registering and combining each most recently acquired image with the previously acquired registered noisy images, and stops the one or more processors to stop the series of images.

9. The system of claim 5, wherein the one or more processors are further programmed to:
  zoom the displayed Region Of Interest.

10. The system of claim 5, wherein combining the most recently acquired noisy image with the previously acquired image includes superimposing the registered most recently acquired image on at least one previously acquired registered noisy image.

11. The system of claim 10, wherein the at least one previously acquired registered noisy image includes a plurality of the previously acquired registered noisy images which have been combined.

12. The system of claim 5, wherein a contrast agent is periodically injected into the vessel such that in the most recently acquired noisy image after injection of the contrast agent, the tip is obscured by the contrast agent and wherein the combining step includes with the one or more processors, combining the most recently acquired noisy image with at least one previously acquired noisy image in which the centerline of the tip is depicted.

13. The system of claim 5, wherein calculating the motion vectors with the one or more processors is further based on a breathing characteristic and a heart pulse characteristic.

14. A medical examination imaging apparatus comprising:
  a diagnostic imaging device that acquires the sequence of noisy medical images in real time; and
  a viewing system according to claim 5 which processes and displays series of images.

* * * * *